US005861314A

United States Patent [19]
Philip et al.

[11] Patent Number: 5,861,314
[45] Date of Patent: Jan. 19, 1999

[54] ADENO-ASSOCIATED VIRAL (AAV) LIPOSOMES AND METHODS RELATED THERETO

[75] Inventors: Ramila Philip, Redwood City; Jane Lebkowski, Portola Valley, both of Calif.

[73] Assignee: Rhône-Poulenc Rorer Pharmaceuticals Inc., Collegeville, Pa.

[21] Appl. No.: 471,603

[22] Filed: Jun. 6, 1995

Related U.S. Application Data

[62] Division of Ser. No. 120,605, Sep. 13, 1993, abandoned.

[51] Int. Cl.$^6$ .................................................. C12N 5/10
[52] U.S. Cl. ..................................... 435/372.3; 435/172.3
[58] Field of Search ............................ 435/69.1, 172.3, 435/172.1, 320.1, 240.2, 366, 372, 372.3; 424/93.6, 450

[56] References Cited

U.S. PATENT DOCUMENTS

| | | | |
|---|---|---|---|
| 4,394,448 | 7/1983 | Szoka, Jr. et al. | 435/172.3 |
| 4,935,372 | 6/1990 | Goh | 435/317.1 |
| 5,126,132 | 6/1992 | Rosenberg | 424/85.2 |
| 5,139,941 | 8/1992 | Muzyczka et al. | 435/69.1 |
| 5,198,344 | 3/1993 | Croop et al. | 435/69.1 |
| 5,250,431 | 10/1993 | Rudd et al. | 435/372.3 |
| 5,252,479 | 10/1993 | Srivastava et al. | 435/235.1 |
| 5,436,146 | 7/1995 | Shenk et al. | 435/172.3 |
| 5,587,308 | 12/1996 | Carter et al. | 435/240.2 |

FOREIGN PATENT DOCUMENTS

| | | |
|---|---|---|
| A 59676/86 | 12/1986 | Australia . |
| 0 405 867 A1 | 1/1991 | European Pat. Off. . |
| A 61-052286 | 3/1986 | Japan . |
| WO 87/00054 | 1/1987 | WIPO . |
| WO 90/10059 | 9/1990 | WIPO . |
| WO 90/13629 | 11/1990 | WIPO . |
| WO 91/05037 | 4/1991 | WIPO . |
| WO 93/09239 | 5/1993 | WIPO . |
| WO 93/15201 | 8/1993 | WIPO . |
| WO 93/24641 | 12/1993 | WIPO . |

OTHER PUBLICATIONS

Faller, D.V. and Baltimore, D., *J. Virol.*, 49:269–272 (1984).
Felgner, P.L. et al., *Proc. Natl. Acad. Sci. USA*, 84:7413–7417 (1987).
Rose, J.K. et al., *Biotechniques*, 10:520–525 (1991).
Malone, R. et al.,*Proc. Natl. Acad. Sci. USA*, 86:6077–6081.
Innes, C.L. et al., *J. Virol.*, 64:957–961 (1990).
Philip, R. et al., *J. Biol. Chem.*, 268:16087–16090 (1993).
Shaefer–Ridder, M. et al., *Science*, 215:166–168 (1982).
Stribling, R. et al., *Proc. Natl. Acad. Sci. USA*, 89:11277–11281 (1992).
Zhu, N. et al., *Science*, 261:209–211 (1993).
Stewart, M.J. et al., *Human Gene Therapy*, 3:267–275 (1992).

Felgner et al., *Nature*, 337:387–388 (1989).
Wang et al., *Proc. Natl. Acad. Sci.*, 84, 7851–7855 (1987).
Kotin, R.M. et al., *Proc. Natl. Acad. Sci.*, 87:2211–2215 (1990).
Hermonat, P.L. et al., *J. Virol.*, 51:329–339 (1984).
Graham, F.L. et al., *J. Gen. Virol.*, 36:59–72 (1977).
Hermonat, P.L. and Muzyczka, N., *Proc. Natl. Acad. Sci. USA*, 81:6466–6470 (1984).
Tratschin, J.D. et al., *Mol. Cell. Biol.*, 5:3251–3260 (1985).
Philip, R. et al., *Mol. Cell. Biol.*, 14(4):2411–2418 (1994).
Lebkowski, J.S. et al.,*Mol. Cell. Biol.*, 8:3988–3996 (1988).
West, W.H. et al., *N. Engl. J. Med.*, 316:898 (1987).
Topolian, S.L. et al., *J. Immunol. Methods*, 102:127–141 (1987).
Hug et al., *Biochem. Biophys. Acta.*, 1097:1–17 (1991).
Marshall, *Science*, 269:1050–1055 (1995).
Hodgson, *Exp. Opin. Ther. Pat.*, 5(5):459–468 (1995).
Miller et al., *F.A.S.E.B.*, 9:190–199 (1995).
Culver et al., *T.I.G.*, 10(5):174–178 (1994).
Rosenberg et al., *Annals Surg.*, 218(4):455–464 (1993).
Gutierrez et al., *Lancet*, 339:715–721 (1992).
Oken, *Am. J. Clin. Oncol. (CCT)*, 5:649–655 (1982).
Rosenberg, S., *Cancer Res.*, (Suppl.)51, 5074s–5079s (1991).
Crystal, R., *Science*, 270, 404–410 (1995).
Mulligan, R., *Science*, 260, 926–930 (1993).
Coghlan et al., *New Scientist*, 14–15 (1995).
Brown, D., *The Washington Post*, A22 (Dec. 8, 1995).
Barinaga, M., *Science*, 266, 1326 (1994).
Cohen, J.S., *Trends in Biotechnolgoy*, 10:87–91 (1992).
Dropulic, B. et al., *Human Gene Therapy*, 5:927–939 (1994).
Pizzo, P.A. et al., *Clinical Infectious Diseases*, 19:177–196 (1994).
Kern, E.R., *Antiviral Agents and Viral Diseases of Man*, 3rd edition, G.J. Galasso et al. editors, pp. 94–95 (1990).
*Sacramento Bee*, p. A22 (Feb. 26, 1994).
*Sacramentao Bee*, p. B5 (Nov. 29, 1991).
Collins, H., *Philadelphia Inquirer*,p. A01 (Mar. 6, 1993).
DeNoon, D.J., *IAC Newletter*, DB Accession No. 02944476 (1995).
Tartour, E. et al., *Biomedicine and Pharmacotherapy*, 46:473–484 (1992).
Friedmann, T., *TIG*, 10(6), 210–214 (1994).

*Primary Examiner*—David Guzo
*Attorney, Agent, or Firm*—Synnestvedt & Lechner

[57] ABSTRACT

A composition for genetic manipulation which comprises a liposome comprised of lipid material, and adeno-associated viral (AAV) material. Typically, the AAV material is plasmid, and comprises a terminal repeat of the AAV genome. Methods are disclosed for introducing genetic material into cells by use of AAV liposomes. Accordingly, genetic material was introduced and integrated into stem cells, T cells, primary tumor cells, or tumor cell lines.

5 Claims, 11 Drawing Sheets

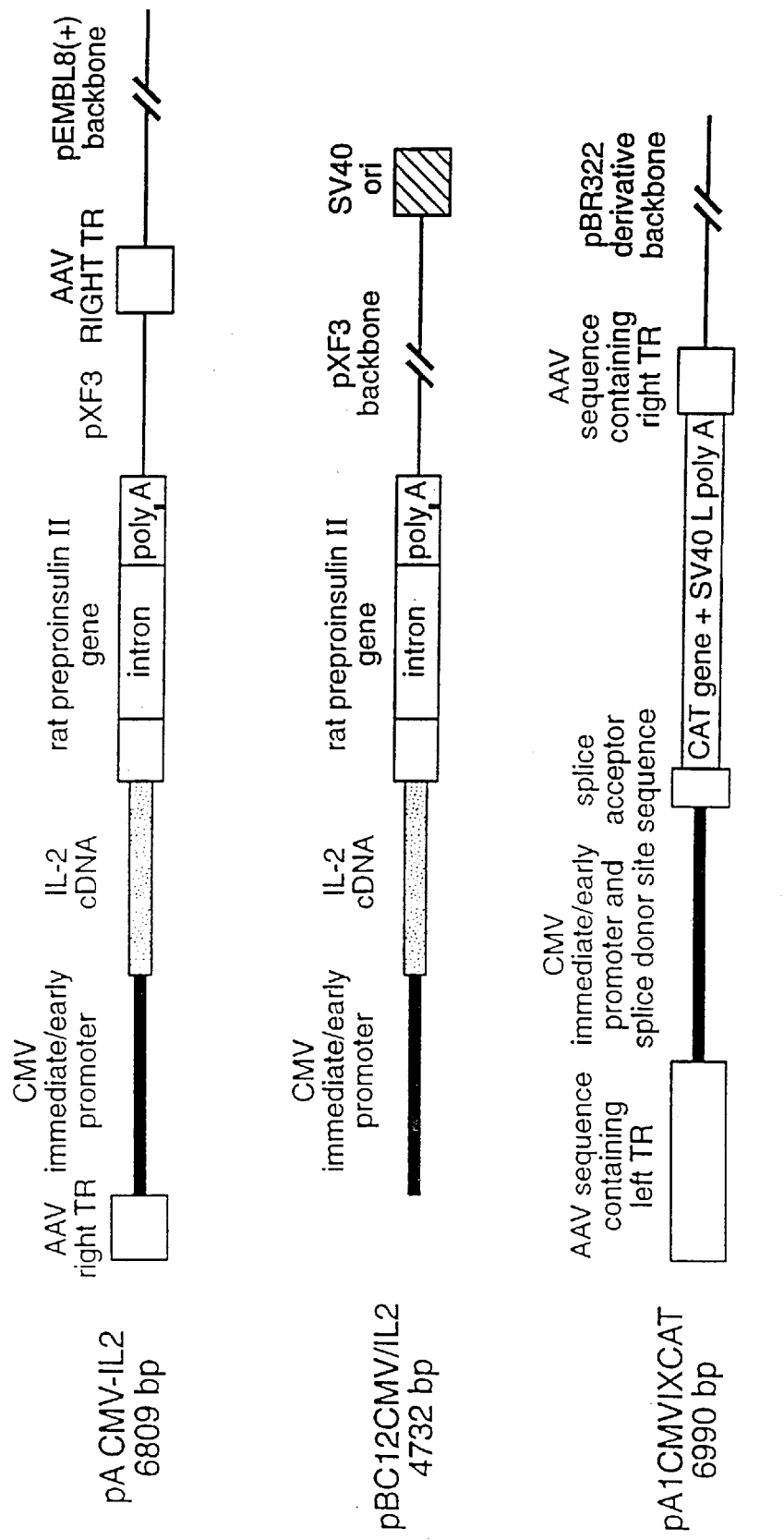
FIG._1

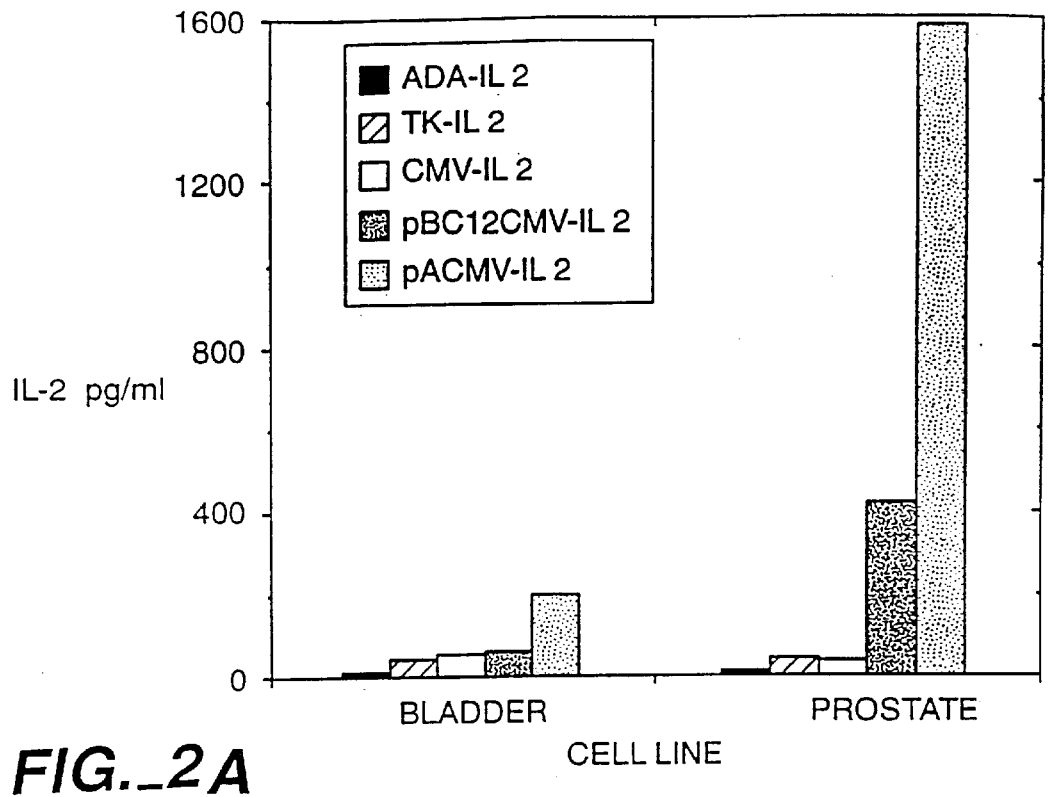
FIG._2A
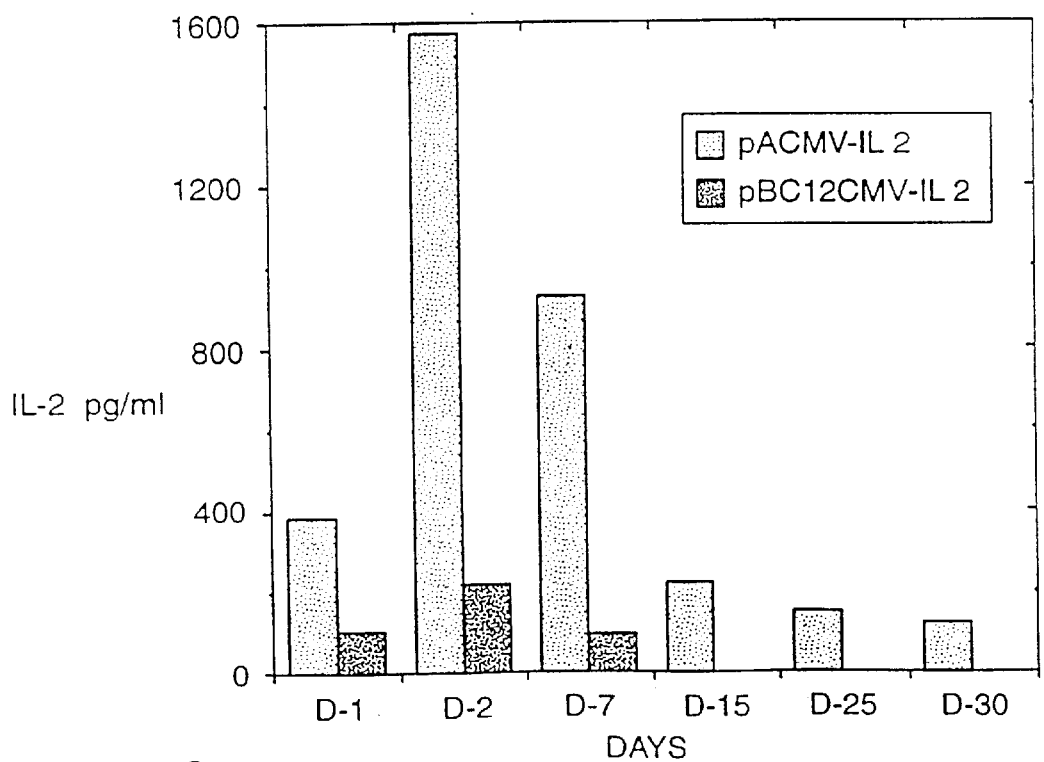
FIG._2B

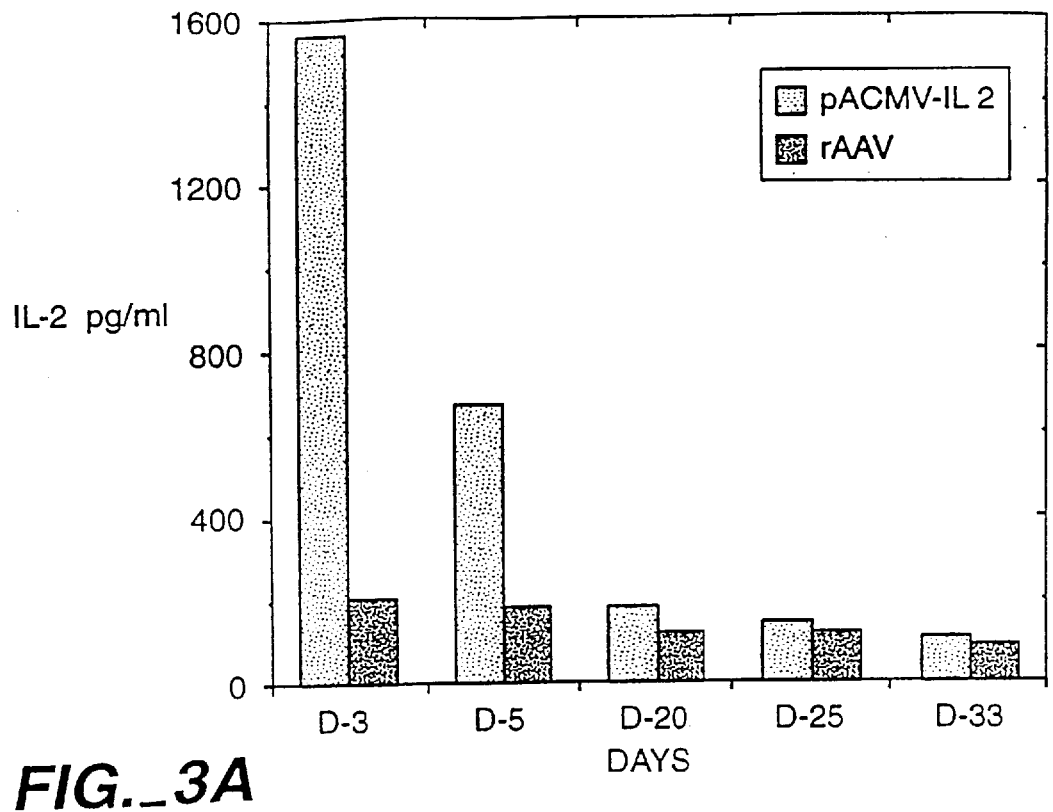
FIG._3A
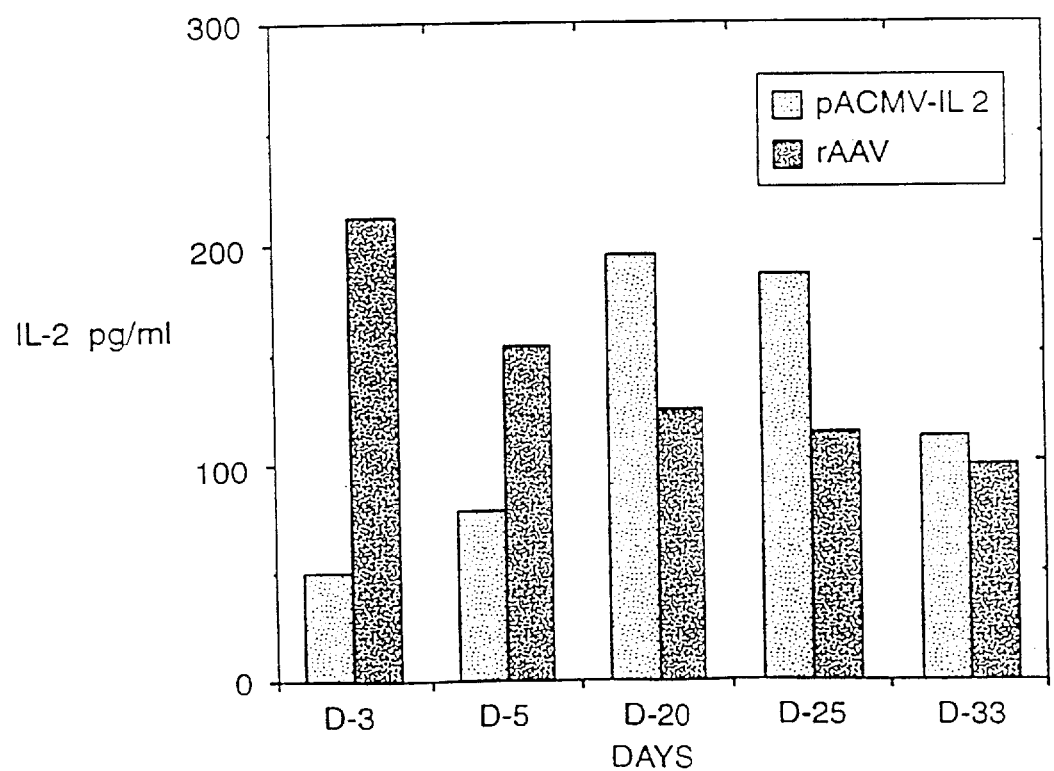
FIG._3B

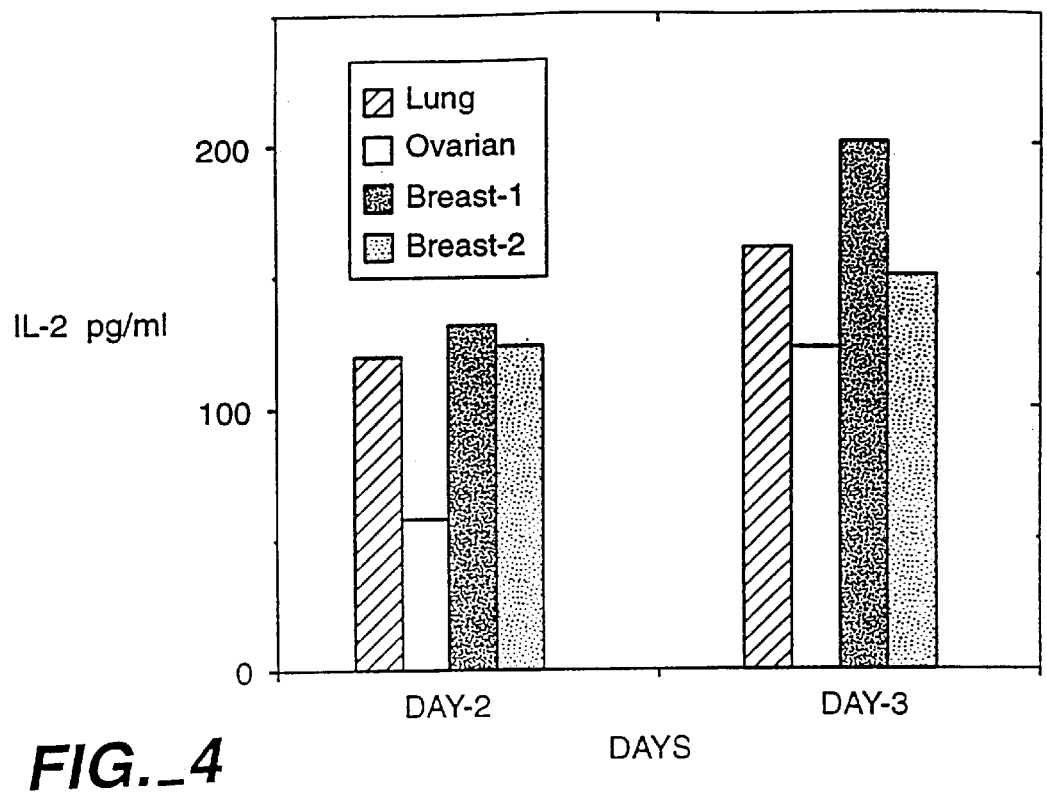
FIG._4
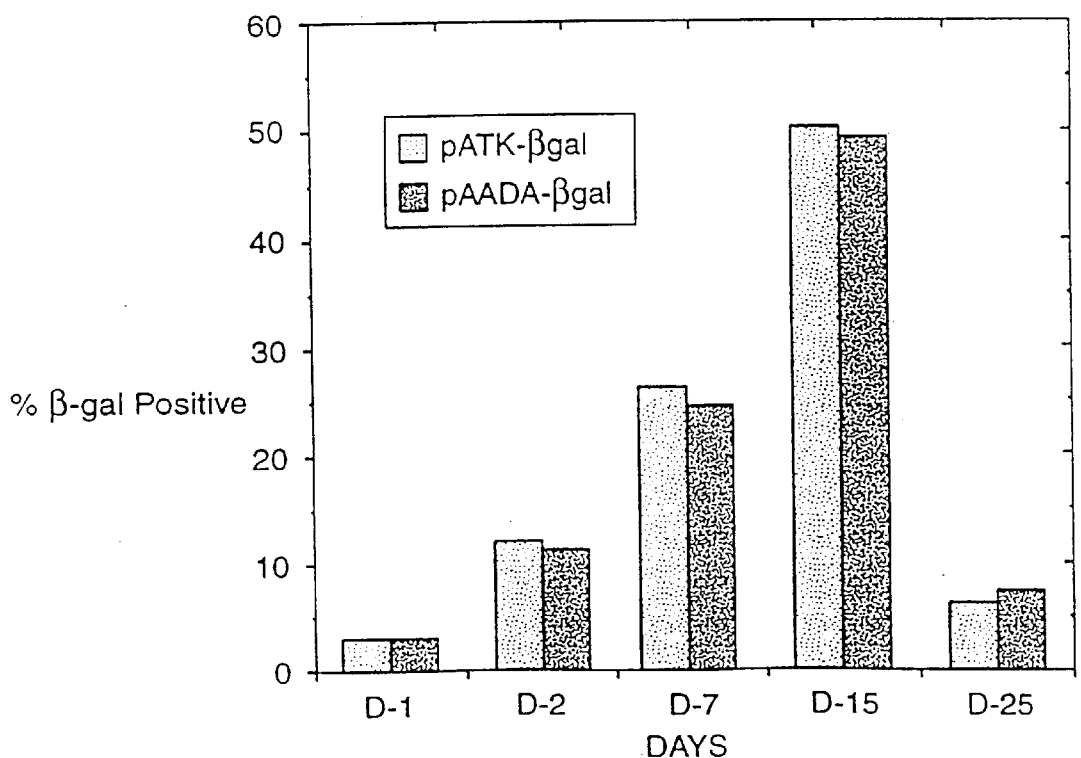
FIG._6

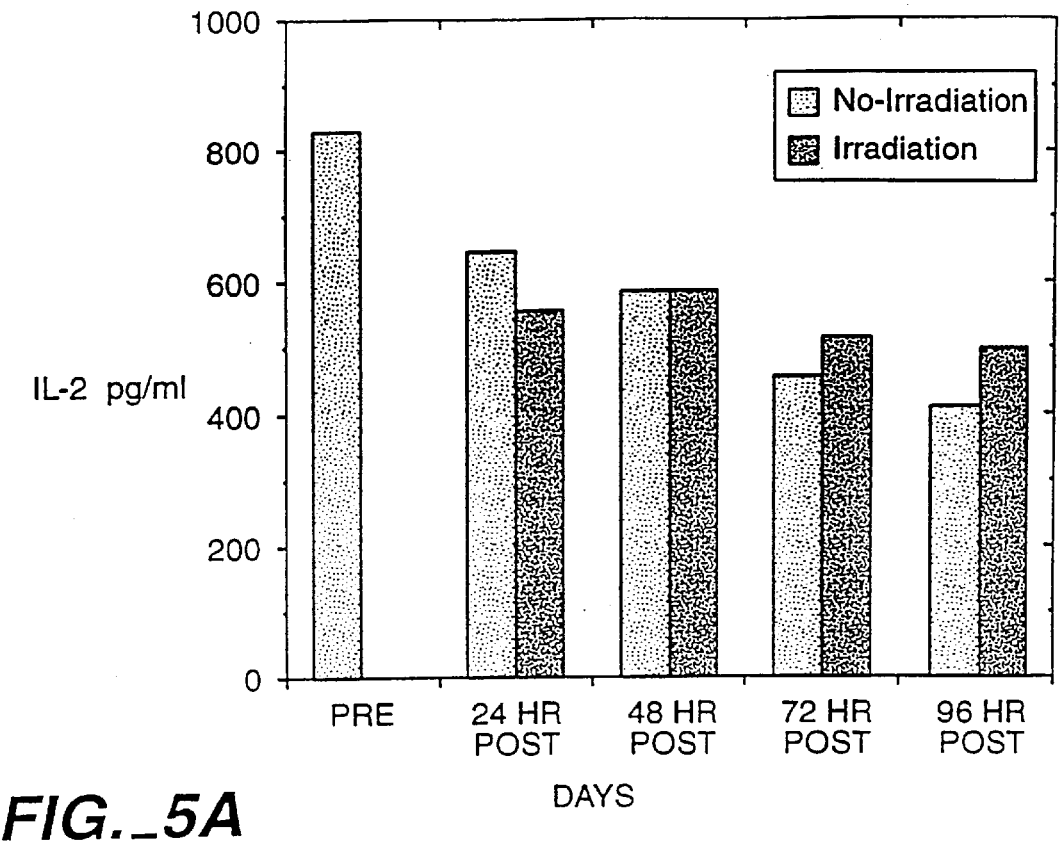
FIG._5A
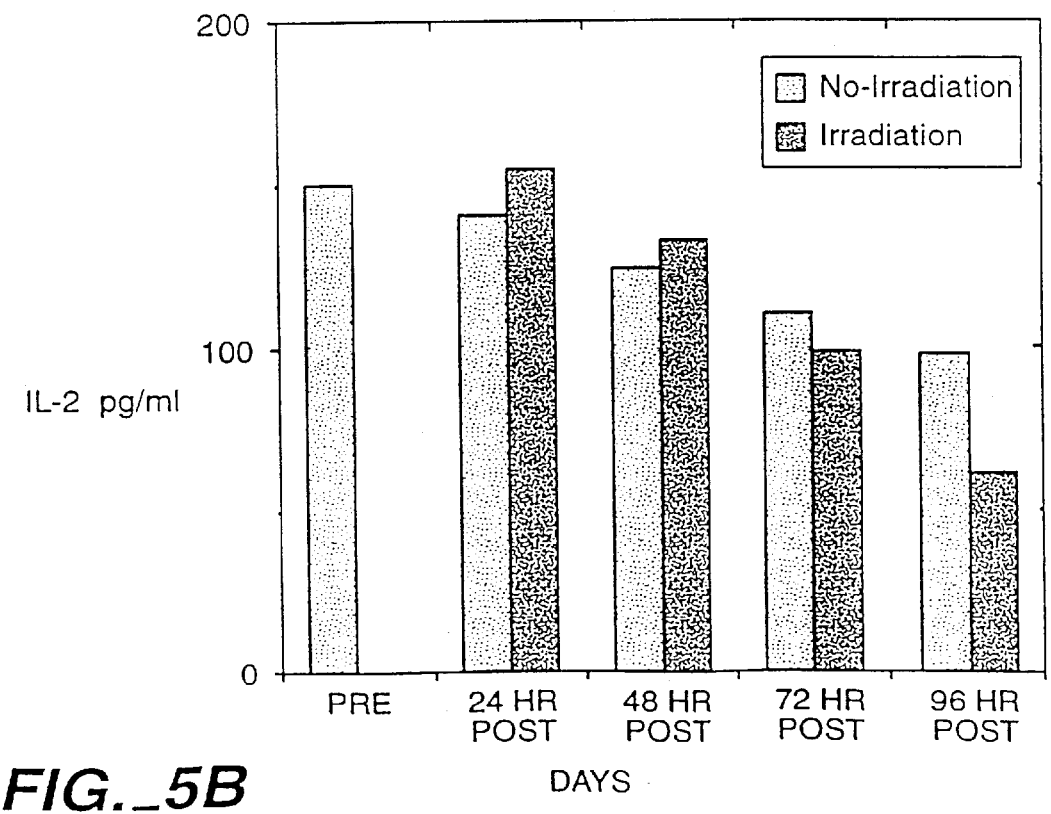
FIG._5B

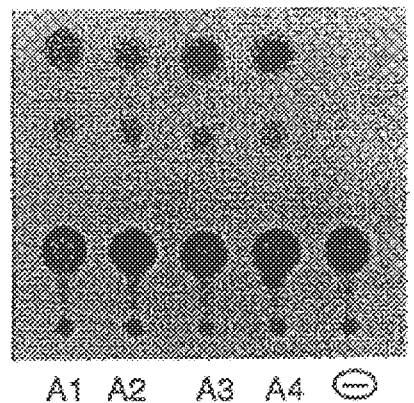
FIG._7A
① 10 μg PACMVIXCAT + 10 nmole D as D:D 1:1
② 10 μg PACMVIXCAT + 20 nmole D as D:D 1:1
③ 10 μg PACMVIXCAT + 10 nmole D as D:C 1:1
④ 10 μg PACMVIXCAT + 20 nmole D as D:C 1:1
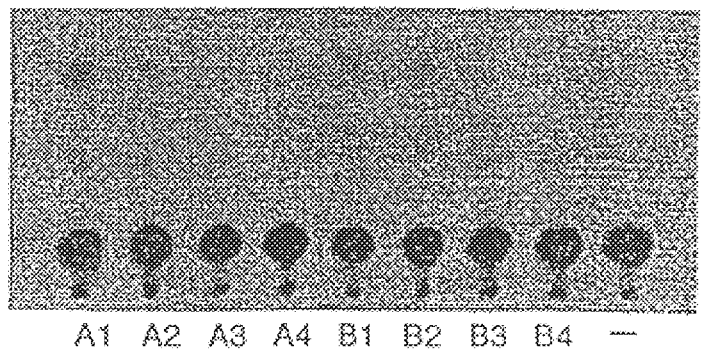
FIG._7B

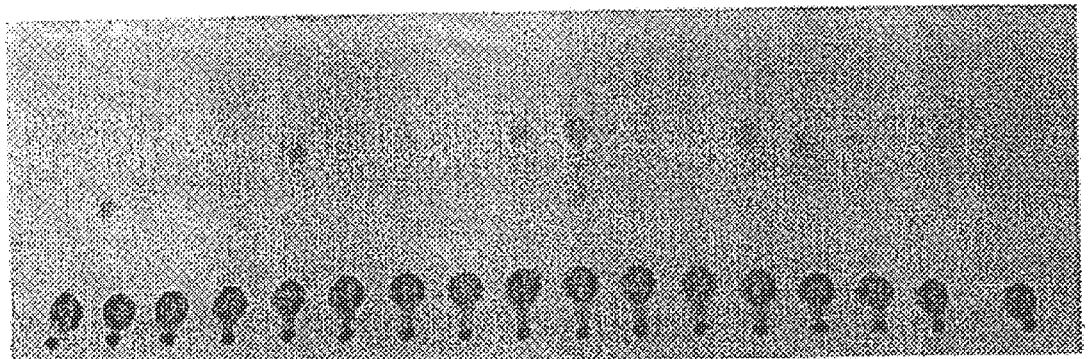
FIG._7C
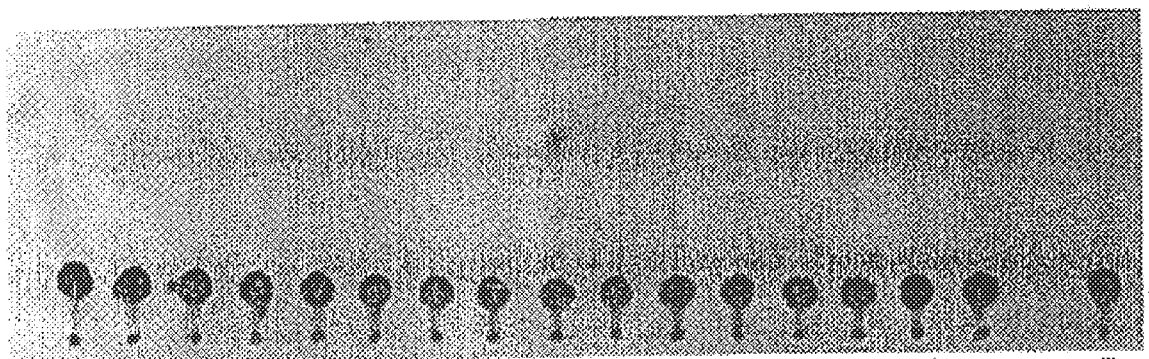
FIG._7D

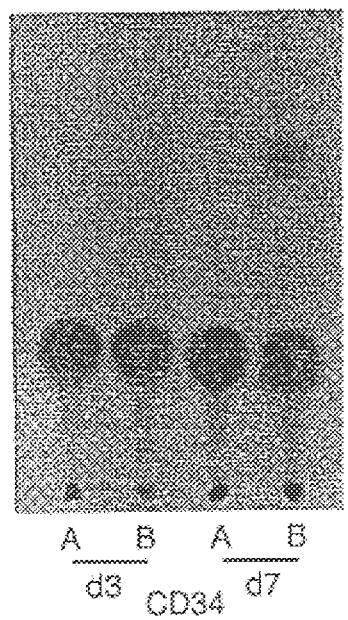
FIG._8

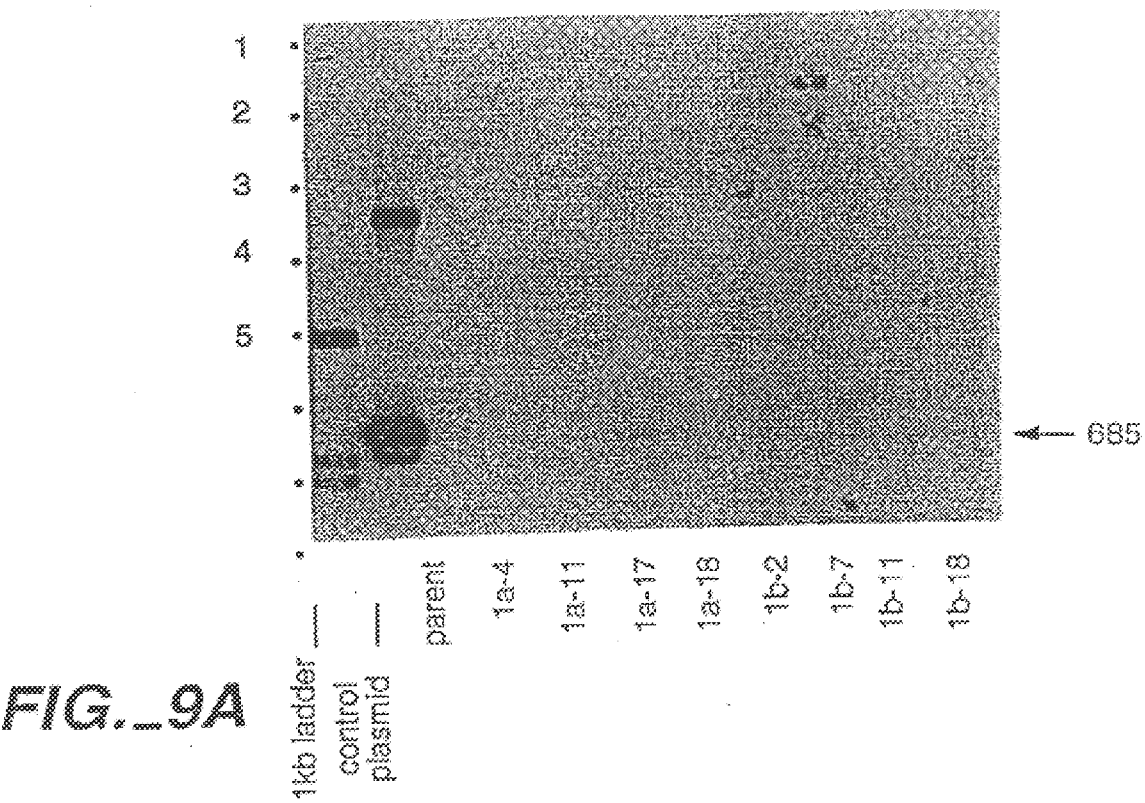
FIG._9A
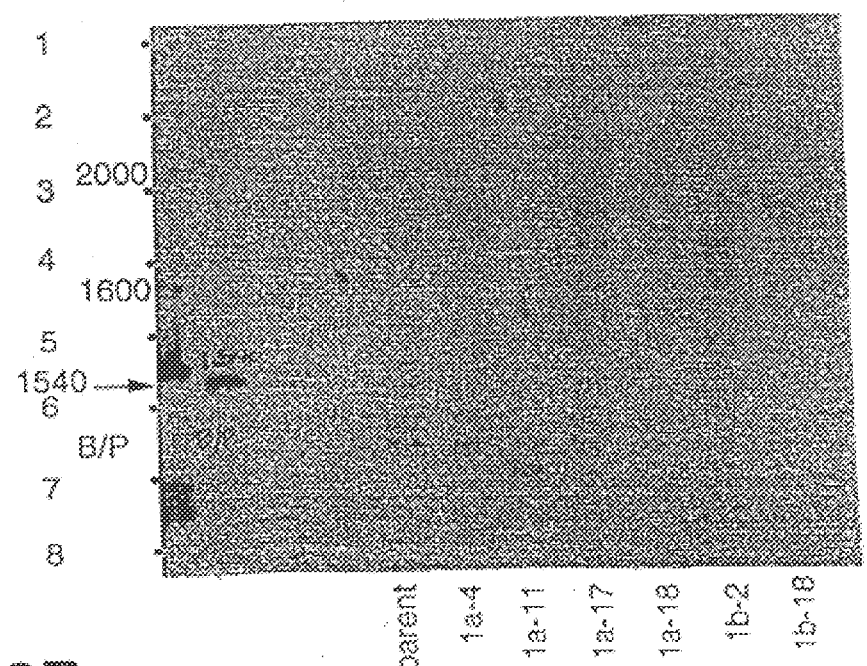
FIG._9B

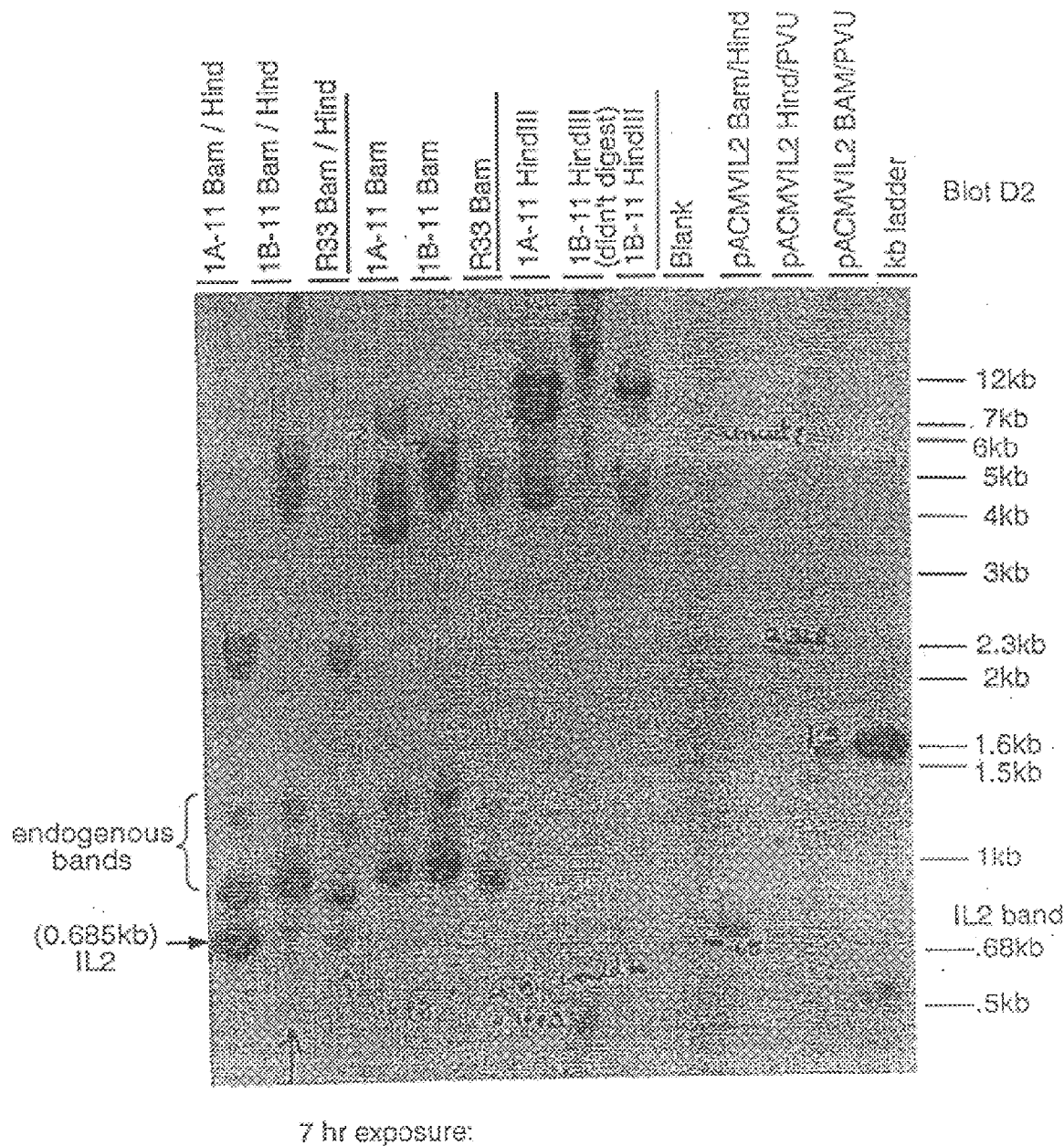
FIG._10A

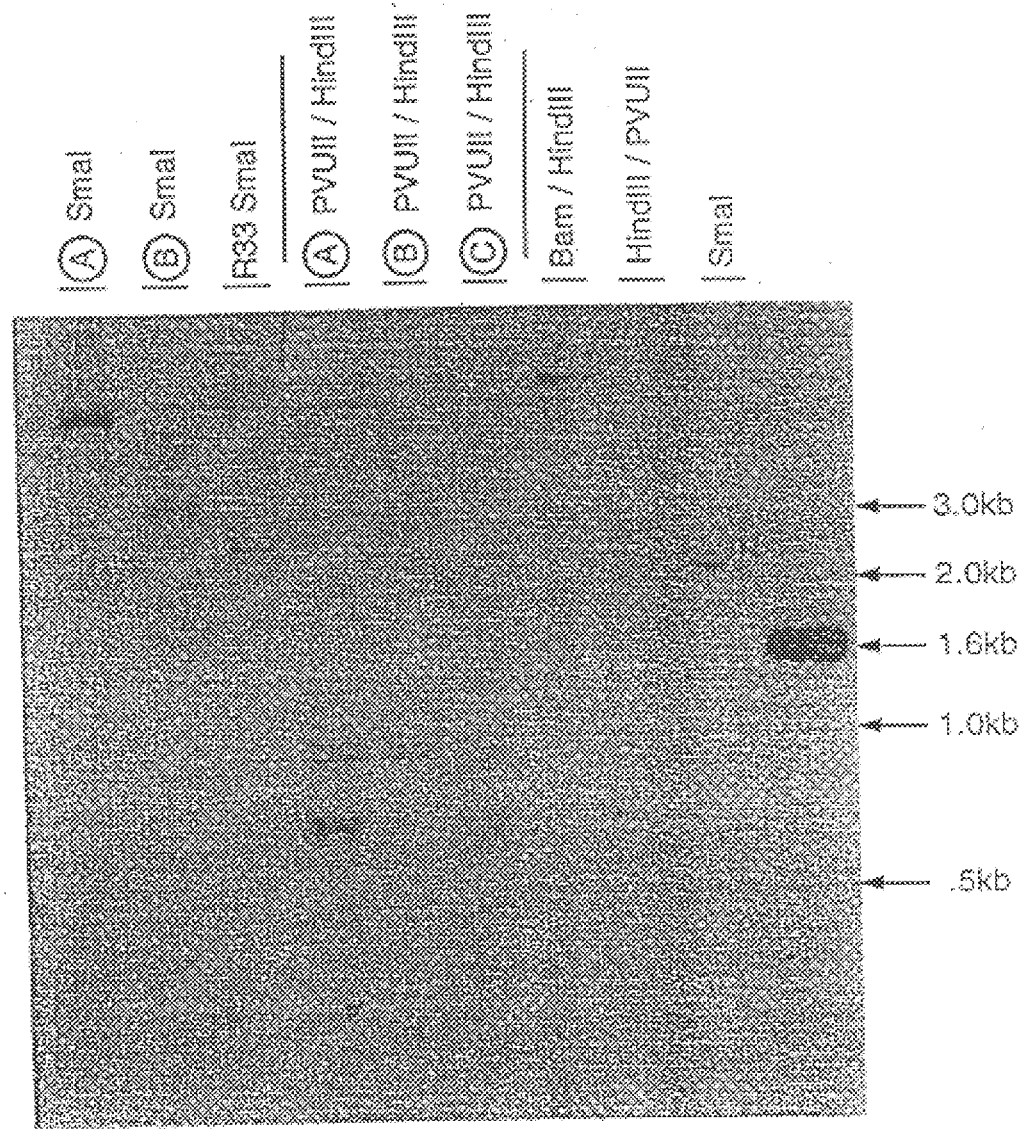
FIG._10B

ADENO-ASSOCIATED VIRAL (AAV) LIPOSOMES AND METHODS RELATED THERETO

This is a division of application Ser. No. 08/120,605 filed Sep. 13, 1993, now abandoned.

TECHNICAL FIELD

The present invention involves cellular manipulation, more particularly it relates to use of cationic liposomes to facilitate transfection by adeno-associated viral (AAV) plasmids.

BACKGROUND ART

Transfection of eukaryotic cells has become an increasingly important technique for the study and development of gene therapy. Advances in gene therapy depend in large part upon the development of delivery systems capable of efficiently introducing DNA into a target cell. A number of methods have been developed for the stable or transient expression of heterologous genes in cultured cell types. These include transduction techniques which use a carrier molecule or virus.

Most gene therapy strategies have relied on transduction by transgene insertion into retroviral or DNA virus vectors (Dimmock, N.J., "Initial stages in infection with animal viruses," *J. Gen. Virol:* (1982) 59:1–22; Duc-Nguyen, H., "Enhancing effect of diethylaminoethyl dextran on the focus forming titer of a murine sarcoma virus (Harvey strain)," *J. Virol.* (1968) 2:643–644). However, adenovirus and other DNA viral vectors can produce infectious sequelae, can be immunogenic after repeated administrations, and can only package a limited amount of insert DNA.

Of the viral vector systems, the recombinant adeno-associated viral (AAV) transduction system has proven to be one of the most efficient vector systems for stably and efficiently carrying genes into a variety of mammalian cell types (Lebkowski, J. S., et al., "Adeno-associated virus: A vector system for efficient introduction and integration of DNA into a variety of mammalian cell types," *Mol. Cell. Biol.* (1988) 3:3988–3996). It has been well-documented that AAV DNA integrates into cellular DNA as one to several tandem copies joined to cellular DNA through inverted terminal repeats (ITRs) of the viral DNA, and that the physical structure of integrated AAV genomes suggest that viral insertions usually appear as multiple copies with a tandem head to tail orientation via the AAV terminal repeats (Kotin, R. M., et al., "Site-specific integration of adeno-associated virus," *Proc. Natl. Acad. Sci.* (1990) 87:2211–2215; Samulski, R. J., et al., "Targeted integration of adeno-associated virus (AAV) into human chromosome 19," *EMBO J.* (1991) 10:3941–3950; Ashktorab, H. and A. Srivastara, "Identification of nuclear proteins that specifically interact with adeno-associated virus type 2 inverted terminal repeat hairpin DNA," *J. Virol.* (1989) 63:3034–3039; Im, D. S., and Muzyczka, N., "Factors that bind to adeno-associated virus terminal repeats," *J. Virol.* (1989) 63:3095–4104; Snyder, R. O., et al., "Evidence for covalent attachment of the adeno-associated virus (AAV) rep protein to the ends of the AAV genome," *J. Virol.* (1990) 64:6204–6213). Thus, the AAV terminal repeats (ITRs) are an essential part of the AAV transduction system.

Although recombinant adeno-associated viral (AAV) vectors differ from adenoviral vectors, the transgene DNA size limitation and packaging properties are the same as with any other DNA viral vectors.

AAV is a linear single stranded DNA parvovirus, and requires co-infection by a second unrelated virus in order to achieve productive infection. AAV carries two sets of functional genes: rep genes, which are necessary for viral replication, and structural capsid protein genes (Hermonat, P. L., et al., "Genetics of adeno-associated virus: Isolation and preliminary characterization of adeno-associated type 2 mutants," *J. Virol.* (1984) 51:329–339; Tratschin, J. D., et al., "Genetic analysis of adeno-associated virus: Properties of deletion mutants constructed in vivo and evidence for an adeno-associated virus replication function," *J. Virol.* (1984) 51:611–619). The rep and capsid genes of AAV can be replaced by a desired DNA fragment to generate AAV plasmid DNA. Transcomplementation of rep and capsid genes are required to create a recombinant virus stock. Upon transduction using such virus stock, the recombinant virus uncoats in the nucleus and integrates into the host genome by its molecular ends (Kotin, R. M., et al., "Site-specific integration of adeno-associated virus," *Proc. Natl. Acad. Sci.* (1990) 87:2211–2215; Samulski, R. J., et al., "Targeted integration of adeno-associated virus (AAV) into human chromosome 19," *EMBO J.* (1991) 10:3941–3950).

Although extensive progress has been made, transduction techniques suffer from variable efficiency, significant concern about possible recombination with endogenous virus, cellular toxicity and immunologic host response reactions. Thus, there is a need for non-viral DNA transfection procedures.

Liposomes have been used to encapsulate and deliver a variety of materials to cells, including nucleic acids and viral particles (regarding nucleic acids, see: Dimmock, N.J., "Initial stages in infection with animal viruses," *J. Gen. Virol:* (1982) 59:1–22; Duc-Nguyen, H., "Enhancing effect of diethylaminoethyl dextran on the focus forming titer of a murine sarcoma virus (Harvey strain)," *J. Virol.* (1968) 2:643–644); regarding viral particles, see: Felgner, P. L., et al., "A highly efficient, lipid-mediated DNA transfection procedure," *Proc. Natl. Acad. Sci. USA* (1987) 84:7413–7417; Faller, D. V. and D. Baltimore, "Liposome encapsulation of retrovirus allows efficient superinfection of resistant cell lines," *J. Virol.* (1984) 49:269–272; Wilson, T., et al., "Biological properties of poliovirus encapsulated in lipid vesicles: Antibody resistance and infectivity in virus resistant cells," *Proc. Natl. Acad. Sci. USA* (1977) 74:3471–3475).

Preformed liposomes that contain synthetic cationic lipids have been shown to form very stable complexes with polyanionic DNA (Felgner, P. L., et al., "A highly efficient, lipid-mediated DNA transfection procedure," *Proc. Natl. Acad. Sci. USA* (1987) 84:7413–7417; Rose, J. K., et al., "A new cationic liposome reagent mediating nearly quantitative transfection of animal cells," *Biotechniques* (1991) 10:520–525). Cationic liposomes, liposomes comprising some cationic lipid, that contained a membrane fusion-promoting lipid distearoyl-phosphatidyl-ethanolamine (DSPE) have efficiently transferred heterologous genes into eukaryotic cells (Felgner, P. L., et al., "A highly efficient, lipid-mediated DNA transfection procedure," *Proc. Natl. Acad. Sci. USA* (1987) 84:7413–7417; Rose, J. K., et al., "A new cationic liposome reagent mediating nearly quantitative transfection of animal cells," *Biotechniques* (1991) 10:520–525). Cationic liposomes can mediate high level cellular expression of transgenes, mRNA (Malone, R., et al., "Cationic liposome mediated RNA transfection," *Proc. Natl. Acad. Sci. USA* (1989) 86:6077–6081), or transcription factors (Debs, R., et al., "Regulation of gene expression in vivo by liposome-based delivery of a purified transcription factor," *J. Biol. Chem.* (1990) 265:10189–10192), by delivering them into a wide variety of cultured cell lines noted in these citations.

Ecotropic and amphotropic packaged retroviral vectors have been shown to infect cultured cells in the presence of cationic liposomes, such as Lipofectin (BRL, Gaithersburg, Md.), and in the absence of specific receptors (Innes, C. L., et al., "Cationic liposomes (Lipofectin) mediate retroviral infection in the absence of specific receptors," *J. Virol.* (1990) 64:957–961).

Overall, cationic liposomes have been shown to spontaneously complex with plasmid DNA or RNA in solution; the liposome comprising nucleic acids then facilitates fusion with cells in culture, resulting in the efficient transfer of nucleic acids to a wide variety of eukaryotic cell types. Liposome vectors are not subject to the DNA size and packaging properties that limit recombinant AAV vectors and adenoviral vectors. Thus, viral infection has been enhanced by coating virus with cationic liposomes and efficiently delivering the virus into cells.

Even though non-viral techniques have overcome some of the problems of the viral systems, there remains a need for improved transfection efficiency in non-viral systems (Hug, P. and R. G. Sleight, "Liposomes for the transformation of eukaryotic cells," *Biochem. Biophys. Acta* (1991) 1097:1–22; Felgner, P. L., et al., "A highly efficient, lipid-mediated DNA transfection procedure," *Proc. Natl. Acad. Sci. USA* (1987) 84:7413–7417). To a certain extent, improved efficiency is attained by the use of promoter enhancer elements in the plasmid DNA constructs (Philip, R., et al., "In vivo gene delivery: Efficient transfection of T lymphocytes in adult mice,;" *J. Biol. Chem.* (1993) 28:16087–16090).

DISCLOSURE OF INVENTION

Cationic liposomes were used to facilitate adeno-associated viral (AAV) plasmid transfections of primary and cultured cell types. AAV plasmid DNA, complexed with liposomes showed several-fold higher levels of expression than complexes with standard plasmids. In addition, expression lasted for a period of 30 days without any selection. AAV plasmid:liposome complexes induced levels of transgene expression that were comparable to those obtained by recombinant AAV transduction. High level gene expression was observed in freshly isolated $CD4^+$ and $CD8^+$ T cells, and $CD34^+$ stem cells from normal human peripheral blood.

Primary breast, ovarian and lung tumor cells were transfected using the AAV plasmid DNA:liposome complexes. Transfected tumor cells were able to express transgene product after lethal irradiation. Transfection efficiency ranged from 10–50% as assessed by β-galactosidase gene expression. The ability to express transgenes in primary tumor cells is utilized to produce tumor vaccine and to produce lymphoid cells that permit highly specific modulations of the cellular immune response in cancer and AIDS, and in gene therapies.

Thus, a composition for genetic manipulation is disclosed. The composition comprises a liposome, itself comprising lipid material, and adeno-associated viral material. The lipid material may itself comprise cationic lipid material. The adeno-associated viral material can comprise an inverted terminal-repeat of the AAV genome. The AAV material can be an AAV plasmid. Furthermore, the AAV material can have two inverted terminal repeats and a promoter, such as a CMV immediate-early early promoter, a CMV immediate-late promoter, an ADA promoter or a TK promoter can be used. Additionally, a composition for genetic manipulation in accordance with the invention can comprise genetic material of interest, typically, transgene material. The transgene material can be placed between two inverted terminal repeats of the AAV plasmid. Cells transfected by a composition in accordance with the invention are also disclosed.

Moreover, a method for introducing genetic material of interest into a cell is disclosed. The method comprises steps of providing a liposome comprising adeno-associated viral material and genetic material of interest. The AAV:liposome complex is then cultured with a host cell, whereby the genetic material of interest is introduced into the host cell. The host cell can be $CD34^+$ stem cells, T cells, primary tumor cells, or cells of a tumor cell line, such as rat bladder (MBT-2), or a rat prostate cell line (R3327). Additionally, a method in accordance with the invention can be used to integrate genetic material of interest into the genetic material of a host cell.

BRIEF DESCRIPTION OF DRAWINGS

FIG. 1. Plasmid maps of three plasmids used in the present studies. The plasmid pACMV-IL2 contained the CMV promoter, IL-2 cDNA and Rat preproinsulin and SV40 polyadenylation sequences identical to pBC12/CMV-IL2 plasmid, additionally pACMV-IL2 also had AAV inverted terminal repeats (ITRs) at both ends. The plasmid pA1CMVIX-CAT was constructed with CMV promoter and CAT gene inserted between the two AAV ITRs.

FIGS. 2a–b. FIG. 2a depicts the levels of gene expression induced by plasmid DNA:liposome complexes. Various IL-2 plasmid constructs were tested for their capability to induce gene expression with a rat bladder and a rat prostate cell line, when the constructs were complexed with liposomes. In both cell lines, the AAV plasmid construct showed the highest level of expression. The levels are expressed as picogram per ml per $10^6$ cells. FIG. 2b depicts the time-course of gene expression induced by AAV plasmid:liposome complexes. To compare the duration of transgene expression, the prostate cell line was transfected with the AAV plasmid (pACMV-IL2) and the corresponding control plasmid (pBC12/CMV-IL2) complexed with liposomes. Supernatants were collected at various time points and assayed for IL-2 levels using an ELISA. IL-2 levels are expressed as picogram/ml/$10^6$ cells in 24 hrs of culture.

FIGS. 3a–b. A comparison of AAV plasmid:liposome complex mediated transfection to recombinant AAV transduction. To determine whether the levels of gene expression induced by AAV plasmid:liposome complexes were equivalent to rAAV transduction, the prostate cell line (FIG. 3a) and bladder line (FIG. 3b) were used to compare the transfection and transduction of IL-2 gene. IL-2 levels were assessed using an ELISA. The levels are expressed as picogram/ml/$10^6$ cells in 24 hrs of culture.

FIG. 4. Expression of IL-2 gene by lipofection with AAV plasmid:liposome complexes of various primary tumor cells. One lung, one ovarian, and two breast tumor samples were isolated from fresh tumor biopsies. IL-2 levels were measured using an ELISA. The levels are indicated as picogram/ml/$10^6$ cells in 24 hrs of culture.

FIGS. 5a–b. Expression of IL-2 by cells transfected in accordance with the invention, then subjected to lethal irradiation. To determine the effect of irradiation on gene expression, the prostate cell line (FIG. 5a) and primary breast cells (FIG. 5b) were transfected and assessed for gene expression after lethal irradiation, as described herein.

Supernatants were collected 24, 48, 72 and 96 hrs after irradiation and tested for IL-2 levels. IL-2 levels are expressed as pg/ml/$10^6$ cells in 24 hr culture.

FIG. 6. Efficiency of AAV:liposome transfection as measured by β-gal gene expression. The β-gal reporter gene was used to assess the transfection efficiency on a per cell basis. The prostate cell line was used for transfection, as described herein. The data is represented as percent of cells positive for fluorescence.

FIGS. 7a–d. Thin layer chromatography studies depicting transfected T lymphocytes. Blood was obtained from donors referred to as A or B. Donor's A or B peripheral blood was used to isolate T cells, and for transfection. Primary T cells freshly isolated from a donor's peripheral blood were tested for transgene expression using AAV plasmid DNA:liposome complexes. T lymphocytes were fractionated as CD3$^+$ (FIG. 7a), or CD5/8$^+$ (FIG. 7b), or as CD4$^+$ (FIG. 7c) or CD8$^+$ (FIG. 7d) populations using AIS MicroCELLector devices. The relevant cells were captured and cultured as described herein. Thereafter, 5–10×$10^6$ cells were plated and transfected with 50 micrograms of AAV plasmid DNA and 50 or 100 nmoles of liposomes to obtain 1:1 or 1:2 DNA:liposome ratios. The cells were harvested 3 days after transfection. Normalized protein content from the extracts were assayed for CAT activity using a chromatographic assay.

FIG. 8. Thin layer chromatography of peripheral blood CD34$^+$ stem cells transfected with AAV plasmid:liposomes. The cells were harvested on Day 3 and Day 7 after transfection. Normalized protein content from the extracts were assayed for CAT activity using a chromatographic assay.

FIGS. 9a–b. Enhanced chemiluminescence (ECL) Southern analysis of genomic DNA from clones transfected with AAV plasmid DNA:liposome complexes. In FIG. 9a, samples were digested with Bam HI and Hind III and probed with IL-2. For the data in FIG. 9b, samples were digested with Bam HI and probed with IL-2. All clones analyzed show presence of IL-2 gene, as demonstrated by the 0.685 kb bands. For FIGS. 9a–b:

lane 1: 1kb ladder
lane 2: plasmid cut with Bam HI/HindIII (9a) and BamHI/pvuII/pvuII (9b).
lane 3: R33 untransfected
lanes 4–11: clones FIGS. 10a–b. Southern analysis ($^{32}$P) of clone 1A11 and 1B11. After Southern blotting, the filter depicted in FIG. 10a was probed with a 0.68 kb IL2 Bam HI/Hind III fragment of pACMV-IL-2. For FIG. 10a:

lane 1: clone 1A11 cut with Bam HI/Hind III
lane 2: clone 1B11 cut with Bam HI/Hind III
lane 3: clone R33 cut with Bam HI/Hind III
lane 4: clone 1A11 cut with Bam HI
lane 5: clone 1B11 cut with Bam HI
lane 6: clone R33 cut with Bam HI
lane 7: clone 1A11 cut with Hind III
lane 8: clone 1B11 cut with Hind III
lane 9: clone R33 cut with Hind III
lane 10: left empty
lane 11: pACMV-IL2 plasmid cut with Bam HI/Hind III
lane 12: pACMV-IL2 plasmid cut with Hind III/pvuII
lane 13: pACMV-IL2 plasmid cut with Bam HI/pvuII For the data shown in FIG. 10b, the filter was probed with a 0.85 kb pvuII/HindIII (AAV ITR/CMV) fragment of the plasmid pACMV-IL2. For FIG. 10b:

lane 1: clone 1A11 cut with smaI
lane 2: clone 1B11 cut with smaI
lane 3: clone R33 cut with smaI
lane 4: clone 1A11 cut with pvuII/Hind III
lane 5: clone 1B11, cut with pvuII/Hind III
lane 6: clone R33, cut with pvuII/Hind III
lane 7: pACMV-IL2, cut with Bam HI/Hind III
lane 8: pACMV-IL2, cut with Hind III/pvuII
lane 9: pACMV-IL2, cut with smaI
lane 10: 1kb ladder

MODES FOR CARRYING OUT THE INVENTION

The studies, disclosed for the first time herein, examined the transportation into cells of AAV plasmid DNA by a system that does not involve viral transduction. Alternatively, a method in accordance with the invention efficiently transfected several mammalian cell types by use of liposomes comprising AAV material. The present invention relates to transfection, and utilizes the elegant carrier system of lipofection together with the proficient transduction capability of the AAV plasmid construct. Advantageously, cationic liposomes were used as a means to facilitate the entry of AAV plasmid DNA into cells in the absence of rep and capsid transcomplementation, recombinant virus or wild type AAV. A lipofection method in accordance with the invention was evaluated to assess the efficiency of gene expression. The present data established the ability to transfect unmodified stem cells, unmodified primary lymphoid cells such as T cells, a variety of freshly isolated tumor cells, and cultured mammalian cell types, with high efficiency for both transient and sustained expression of DNA. The ability to efficiently transfect unmodified T cells and unmodified stem cells is disclosed for the first time in the art.

I. SOURCE MATERIALS AND METHODS EMPLOYED

A. Cell Lines.

A rat prostate cell line (R3327) and rat bladder cell line (MBT-2) were obtained from Dr. Eli Gilboa, Duke University. Both cell lines were maintained in RPMI-1640 medium supplemented with 5% fetal bovine serum (FBS). Cell line 293 is a human embryonic kidney cell line that was transformed by adenovirus type 5, and was obtained from the ATCC (Graham, F. L., et al., "Characteristics of a human cell line transformed by DNA from human adenovirus type 5," *J. Gen. Virol.* (1977) 3:59–72). Cell line 293 was grown in Dulbecco modified eagle medium supplemented with 10% FBS.

B. Cell preparation of Primary Tumor Cells.

Primary lung, ovarian and three breast tumor cells were obtained from solid tumors of patients. The tumor samples were minced into small pieces and digested in 200 ml of AIM V medium (Gibco), supplemented with 450 u/ml collagenase IV (Sigma), 10.8K units/ml DNase I (Sigma), and 2000 u/ml hyaluronidase V (Sigma) (Topolian, S. L., et al., "Expansion of human tumor infiltrating lymphocytes for use in immunotherapy trials," *J. Immunol. Methods* (1987) 102:127–141). After 1–2 hours of digestion, cells were homogenized with a glass homogenizer (Bellco). The cells were washed three times in DPBS-CMF (Whittaker). Lymphocytes were separated from non-lymphoid cells by capture on an AIS MicroCELLector-CD5/8 device (AIS, Santa Clara, Calif.). Nonadherent cells (mainly tumor cells) were removed and cultured in RPMI 1640 supplemented with 2 mM L glutamine, 100 u/ml penicillin-streptomycin, and 10% FBS. Tumor cells were cultured for 2 to 4 weeks prior to transfection.

C. Preparation of Peripheral Blood Mononuclear Cells.

Peripheral blood mononuclear cells (PBMCs) from healthy control patients were isolated from buffy coats (Stanford University Blood Bank, Stanford, Calif.), using Lymphoprep (Nycomed, Norway).

T cells or T cell subsets were further isolated using AIS MicroCELLectors (Applied Immune Sciences, Santa Clara, Calif.). Briefly, PBMCs were resuspended at $15 \times 10^6$ cells per ml in 0.5% Gamimmune (Miles, Inc., Elkhart, Ind.) and loaded onto washed CD3, CD4, CD8, CD5/8, or CD34 AIS MicroCELLectors. After 1 hour, nonadherent cells were removed from the AIS MicroCELLectors. Complete medium, RPMI 1640 (Whittaker) containing 10% fetal bovine serum, 2 mM L-glutamine, and 100 u/ml penicillin/streptomycin was added to the adherent cells in the AIS MicroCELLectors. After 2–3 days in a 5% $CO_2$, 37° C. humidified environment, adherent cells were removed and prepared for transfection.

D. Plasmid Preparation.

A first study plasmid (pACMV-IL2) was used in the present studies; this plasmid contained the human interleukin-2 gene (IL-2) as IL-2 cDNA, and the immediate-early promoter-enhancer element of the human cytomegalovirus (CMV), and Rat preproinsulin and SV40 polyadenylation sequences, flanked by adeno-associated virus inverted terminal repeats (ITRs) at both ends. (This plasmid was provided by Dr. J. Rosenblatt, UCLA, CA; Dr. Rosenblatt's name for the plasmid is pSSV9/CMV-IL2). A corresponding control plasmid pBC12/CMV-IL2, which was identical to pACMV-IL2 but which lacked the AAV terminal repeats, was also used (FIG. 1).

A second study plasmid, pA1CMVIX-CAT, contained the CMV immediate-early promoter enhancer sequences, and an intron derived from pOG44 (Strategene); the bacterial CAT gene; SV40 late polyadenylation signal flanked by AAV terminal repeats in a pBR322 backbone (FIG. 1).

The plasmids pATK-βgal and pAADA-βgal contained the βgal gene linked to either the TK or ADA promoter, respectively, in an AAV plasmid backbone. (βgal plasmids provided by Dr. Eli Gilboa, Duke Univ.) Standard plasmid constructs that contained the IL-2 gene, but that did not contain AAV components were also used. The standard plasmid constructs carried the IL-2 gene, with an adenosine deaminase (ADA), a thymidine kinase (TK) or the immediate-late cytomegalovirus (CMV) promoter. (standard plasmids obtained from ATCC)

TABLE 1

Plasmids Used in Present Studies

| Plasmid Name | Promoter | Genomic Elements |
|---|---|---|
| pACMV-IL2 | CMV (immediate–early) | IL2, AAV |
| pBC12/CMV-IL2 | CMV (immediate–early) | IL2 |
| pA1CMVIX-CAT | CMV (immediate–early) | CAT, AAV |
| pADA-IL2 | ADA | IL2 |
| pTK-IL2 | TK | IL2 |
| pCMV-IL2 | CMV (immediate–late) | IL2 |
| pATC-βgal | TK | βgal, AAV |
| pAADA-βgal | ADA | βgal, AAV |

All plasmids were isolated by alkaline lysis and ammonium acetate precipitation, followed by treatment with DNase-free RNase, phenol/chloroform/isoamyl extractions and ammonium acetate precipitation (Ausubel, F. M., et al., *Current Protocols in Molecular Biology* (John Wiley and Sons, Inc. 1993)).

E. Liposome Preparation.

Small unilamellar liposomes were prepared from the cationic lipid dioctadecyl-dimethyl-ammonium-bromide (DDAB) (Sigma) in combination with the neutral lipid dioleoyl-phosphatidyl-ethanolamine (DOPE) (Avanti Polar Lipids). Lipids were dissolved in chloroform. DDAB was mixed with DOPE in either a 1:1 or 1:2 molar ratio in a round-bottomed flask, and the lipid mixture was dried on a rotary evaporator. The lipid film was rehydrated by adding sterile double distilled water to yield a final concentration of 1 mM DDAB. This solution was sonicated in a bath sonicator (Laboratory Supplies, Hicksville, N.Y.) until clear. The liposomes were stored at 4° C. under argon. For in vivo use of liposomes via intravenous administration a DDAB:DOPE ratio of 1:4 to 1:5 is used; for intraperitoneal administration a DDAB:DOPE ratio of 1:1 to 1:2 is used.

F. Preparation of recombinant AAV (rAAV) for transduction.

For the preparation of recombinant AAV stocks, cells of the cell line 293 were split and grown to approximately 30–50% confluence. Thereupon, the cells were infected with adenovirus type 5 at a multiplicity of infection of 1 to 5, and incubated at 37° C. After 2 to 4 hours, the infected cells were cotransfected with 10 μg of a plasmid comprising a gene of interest and 10 μg of the rep capsid complementation plasmid, pΔBal, per 100 mm tissue culture dish ($0.5-1 \times 10^7$ cells). Calcium phosphate coprecipitation was used for transfection (Hermonat, P. L. and Muzyczka, N., "Use of adeno-associated virus as a mammalian DNA cloning vector. Transduction of neomycin resistance into mammalian tissue culture cells," *Proc. Natl. Acad. Sci. USA* (1984) 81:6466–6470). At 12 to 18 hours after transfection, the medium was removed from the cells and replaced with 5 ml of DMEM medium containing 10% FBS.

At 48 to 72 hours after transfection, AAV was harvested according to the following procedure: Cells and medium were collected together, and freeze thawed three times to lyse the cells. The suspension of cells and medium was then centrifuged to remove cellular debris, and the supernatant was incubated at 56° C. for 1 hour to inactivate adenovirus (Hermonat, P. L. and N. Muzyczka, "Use of adeno-associated virus as a mammalian DNA cloning vector. Transduction of neomycin resistance into mammalian tissue culture cells," *Proc. Natl. Acad. Sci. USA* (1984) 81:6466–6470; Tratschin, J. D., et al., "Adeno-associated virus vector for high frequency integration, expression, and rescue of genes in mammalian cells," *Mol. Cell. Biol.* (1985) 5:3251–3260). After heat inactivation, the viral supernatant was filtered through cellulose acetate filters (1.2 μm). Viral stocks were then stored at −20° C. One milliliter of AAV supernatant was used to transduce $1 \times 10^6$ cells.

G. Cellular Transfection "Lipofection".

For primary tumor cells and both rat tumor cell lines (R3327 and MBT-2), $1 \times 10^6$ cells were plated in 2 ml serum-free medium per well of a 6 well dish. Thereafter, 5 μg of AAV plasmid DNA was mixed with 5 nmoles of DDAB as liposomes composed of DDAB and DOPE in a 1:2 molar ratio, respectively. Serum-free medium (0.5 ml) was added to the AAV:liposome complex, which was then transferred to the cells. To effect lipofection, the cells were incubated at room temperature for 5 minutes, then fetal bovine serum was added to the cells to yield a final concentration of 5% fetal bovine serum.

For T cells, $5-10 \times 10^6$ cells were plated in 1 ml of serum-free medium per well of a 6 well dish. 50 μg of plasmid DNA was mixed with 50 nmoles of DDAB as liposomes composed of DDAB and DOPE in a 1:1 molar ratio. The transfections "lipofections" were then performed as above.

For stem cells, 1–2×10⁶ cells were transfected with complexes comprising 10 micrograms of plasmid DNA and 10 nmoles of liposome. The transfected cells were cultured with medium containing stem cell factor, IL-3 and IL-1. On Day 3 and 7, the cells were harvested and extracts were made.

H. IL-2 Assay.

Cells were counted, and 1×10⁶ cells were plated in 1 ml per well of a 24 well plate. The following day, supernatants were collected and assessed by using a Quantikine IL-2 ELISA kit (R&D Systems, Minneapolis, Minn.). IL-2 levels were defined as picograms/ml of the supernatant.

I. β-galactosidase Assay.

The FluoReporter lacZ gene fusion detection kit from Molecular Probes (Eugene, Oreg.) was used to quantitate lacZ β-D-galactosidase in single cells by measurement of the fluorescence of the enzyme hydrolysis product, fluorescein. The AAV/β-gal plasmids (pATK-βgal and pAADA-βgal) were used with this kit. Fluorescein is produced by enzymatic cleavage of fluorescein di-b-D-galactopyranoside (FDG) in cells that express the marker gene b-D-galactosidase. The cells then were analyzed using flow cytometry (FACScan, Becton Dickinson, San Jose, Calif.)

II. STUDY RESULTS

A. Level of IL-2 gene expression by use of AAV plasmid-:cationic liposome complex.

To evaluate the gene transfer efficiency of AAV plasmids, the IL-2 gene transfer efficiency of AAV plasmids were compared to the efficiencies of standard plasmid constructs. The standard plasmids carried the IL-2 gene, with an adenosine deaminase (ADA) promoter (pADA-IL2), a thymidine kinase (TK) promoter (pTKIL-2), or the immediate-late cytomegalovirus (CMV) promoter (pCMV-IL2). The AAV IL-2 study plasmid (pACMV-IL2) contained the CMV promoter (immediate early), with the IL-2 gene placed downstream of the promoter. (FIG. 1) As shown in FIG. 1, the corresponding control plasmid, the pBC12/CMV-IL2 construct, was identical to pACMV-IL2, but lacked the AAV terminal repeats (ITRs).

All five plasmids containing the IL-2 gene were complexed with liposomes and tested for transfection efficiency on the two cultured tumor cell lines: the rat bladder (MBT-2) and the rat prostate (R3327) cell lines. The cell lines were transfected with 10 micrograms of plasmid DNA complexed to 10 nmoles of liposomes per 1×10⁶ cells. Supernatants were collected on Day 3 and tested for the levels of IL-2 using an IL-2 ELISA kit.

The AAV plasmid (pACMV-IL2) induced the highest levels of expression in both cell lines (FIG. 2a). The IL-2 gene with an ADA promoter (pADA-IL2) induced the least amount of expression in both cell lines. As shown in FIG. 2a, both TK and CMV (immediate-late promoter) IL-2 constructs induced comparable levels of IL-2 expression in both cell lines. However, the pBC12/CMV-IL2 plasmid, which contained CMV immediate-early promoter showed higher levels of gene expression in the prostate cell line when compared to the bladder cell line. Among the plasmids tested, the AAV IL-2 study plasmid induced the highest level of expression in both cell lines, with a significant level of increase observed in the prostate cell line.

As illustrated in FIG. 2b, the duration of expression induced by the corresponding control plasmid (pBC12/CMV-IL2) and the AAV IL-2 study plasmid (pACMV-IL2) in the prostate cell line R3327 were studied. Expression was assessed up to 30 days in these cultures without any selection. The cells were seeded at 1×10⁶/ml and supernatants were collected for analysis every 24 hours. The cells doubled every 48 hours in culture. The data in FIG. 2b indicate that, in addition to the enhanced levels of expression, the duration of expression lasted 30 days post-transfection with AAV plasmid (pACMV-IL2). Notably, significant expression continued throughout the full duration of the time period of evaluation. As shown in FIG. 2b, both plasmids induced maximum levels of expression between Day 2 and Day 7, by Day 15 IL-2 levels declined and then were maintained at approximately 100 pg/ml only in the AAV plasmid transfected group. Similar sustained levels of expression were observed in the bladder cell line, as well as with cells from a primary lung tumor, when AAV plasmid:liposome complexes were used for transfection (data not illustrated).

B. Comparison of AAV plasmid:liposome transfection "lipofection" and recombinant AAV transduction.

The prostate and bladder cell lines were transfected and transduced, to determine whether optimal AAV:liposome transfection was comparable to optimal recombinant AAV transduction. For optimal transfection, 10 micrograms of AAV plasmid DNA was complexed to 10 nmoles of liposomes per 1×10⁶ cells in 2 ml final volume. For maximal rAAV transduction, 2 ml of the viral supernatant was added to 1×10⁶ cells in 1 ml of complete medium. After 24 hrs, the cells were washed and resuspended in fresh complete medium. Supernatant was collected at various time points after transfection and transduction.

In the prostate line (FIG. 3a), transfection induced higher levels of expression than AAV transduction under test conditions (2 ml of viral supernatant for 1×10⁶ cells, versus 10 μg DNA:10 nmoles of liposomes). Although results on Day 3 through Day 5 showed approximately 10-fold higher levels of IL-2 with transfection, by Day 20 comparable levels were observed in both transfected and transduced groups.

Transduction with recombinant AAV initially induced higher levels of IL-2 production in the bladder cell line, as compared to transfection using liposomes (FIG. 3b). Similar to the prostate cell line, the bladder cell line also showed a decline in IL-2 levels by Day 20, with comparable levels of IL-2 produced through Day 33 in both transfected and transduced groups.

C. Transfection of primary tumor cells using AAV plasmid DNA:liposome complexes.

In the foregoing experiments disclosed herein, significant transgene expression was demonstrated in cultured cell lines. In order to assess whether cationic liposome:AAV plasmid DNA complexes also mediated comparable transgene expression in freshly isolated primary tumor cells, cells of four different primary tumors were transfected with the AAV IL-2 study plasmid using liposomes. Tumor cells were cultured in RPMI-1640 medium supplemented with 10% FBS for 2–3 weeks prior to the transfection. The cells were plated to 1×10⁶ cells per ml concentration and transfected with 10 micrograms of DNA complexed with 10 nmoles of liposomes. Supernatants were collected on Day 2 and 3.

As shown in FIG. 4, all four primary cell types produced significant levels of IL-2 after transfection. The highest level of expression was observed on Day 3 during the 10 Day study period (lung and one breast sample were studied for longer periods). IL-2 gene expression was followed in cells of the lung tumor and in cells of one of the breast tumors as long as 25 days after transfection in culture. The levels on Day 15 were equivalent (100 pg/ml IL-2) in both cell lines, and the cells derived from primary tumors. (data not shown)

D. Effect of lethal irradiation on transgene expression.

To determine the effect of irradiation on gene expression, the prostate cell line (FIG. 5a) and cells of a primary breast tumor (FIG. 5b) were transfected and assessed for gene expression after lethal irradiation. Both cell types were transfected using optimal AAV plasmid:liposome complexes. On the second day after transfection, an aliquot of each culture was subjected to 6000 rad using $^{60}$Co irradiator, whereby cellular division is abolished, and the aliquots were then kept in culture. One-half of each culture was maintained as a non-irradiated control. The aliquots were subjected to 6000 rad using a $^{60}$CO irradiator, while the expression level of IL-2 was approximately 300–400 pg/ml. Supernatants were collected 24, 48, 72 and 96 hrs after irradiation, and then tested for IL-2 levels.

As shown in FIGS. 5a–b, lethal irradiation post-transfection did not inhibit transgene expression. Neither the prostate cell line nor the primary tumor cells exhibited any change in IL-2 expression after irradiation. Thus, although cellular division was abolished, IL-2 secretion was not sensitive to irradiation. This is advantageous, since most gene therapy strategies involve gene delivery to primary T lymphocytes, which do not generally divide absent modification, or to tumor cells, as discussed in greater detail below.

E. Level of β-D-galactosidase gene expression by use of AAV plasmid:liposome complex.

To demonstrate the expression levels on a per cell basis, the β-D-galactosidase gene was used for transfection experiments. Each of two AAV β-gal plasmids (pATK-Bgal and pAADA-Bgal) (plasmids obtained from Dr. Eli Gilboa, Duke University) were complexed with cationic liposomes and used for transfection of the prostate cell line. Ten micrograms of pATK-βgal or pAADA-βgal plasmid DNA was complexed with 10 nmoles of liposomes, the complexes were then used to transfect $1 \times 10^6$ cells in 2 ml volume. At various time points, approximately $5 \times 10^5$ cells were harvested and stained with fluorescent substrate FDG and analyzed using flow cytometry.

Maximum transgene expression was observed between Day 7 and Day 15 (FIG. 6). Significant levels of β-gal activity were observed through Day 25. Flow cytometry analysis of β-gal positive cells showed maximal levels of 10 to 50% transfection efficiency with both plasmid constructs. The levels declined to 5 to 10% by Day 25. The expression pattern and duration was similar to that of IL-2 expression set forth above.

F. Transgene expression induced by AAV plasmid:liposome complex in freshly isolated peripheral blood T cell subpodulation.

The effect of AAV plasmid:liposome complex in transfecting freshly isolated human peripheral blood T cell populations was examined. The gene for chloramphenicol acetyl transferase (CAT) enzyme was used as the reporter gene in the pA1CMVIX-CAT plasmid (FIG. 1). The pA1CMVIX-CAT constructs were made using the AAV backbone (pA1) with CMV immediate-early promoter enhancer sequences and CAT gene. Total and purified CD4$^+$ and CD8$^+$ subpopulations of T cells were used for transfections. Both total (CD3 or CD5/8 selected) and purified (CD4 or CD8 selected) subpopulations of T cells (FIGS. 7a–d), as well as CD34$^+$ stem cells (FIG. 8), described in Section G. below, showed significant levels of CAT gene expression.

Primary T cells freshly isolated from peripheral blood were tested for transgene expression using AAV plasmid DNA:liposome complexes. Results of thin layer chromatography assays for CAT activity from CD3$^+$ T cells, CD5/8 selected T cells (total T cells), the CD4$^+$ subpopulation of T cells, and the CD8$^+$ subpopulation of T cells are depicted in FIGS. 7a–d, respectively.

T lymphocytes were fractionated as CD3$^+$, or CD5/8$^+$ or CD4$^+$ or CD8$^+$ populations using AIS MicroCELLector devices. The relevant cells were captured and nonadherent cells were washed off. The adherent cells were removed from the devices after 2 days in culture with RPMI-1640 and 10% FBS. Five to $10 \times 10^6$ cells were plated and transfected with 50 micrograms of AAV plasmid DNA and 50 or 100 nmoles of liposomes to obtain 1:1 or 1:2 DNA:liposome ratios. The cells were harvested 3 days after transfection and the cell extracts normalized by protein content and CAT activity measured using a chromatographic assay. Blood was obtained from Donors referred to as A or B. Peripheral blood of Donor A or B was used to isolate the T cells, and for transfection.

As depicted in FIGS. 7a–d, the lipid composition of the liposomes comprising AAV was varied, as was the ratio of DNA to liposome. In the study of CD3$^+$ T cells (FIG. 7a) cells from one donor (Donor A) were employed. For the studies of CD5/8 selected T cells (FIG. 7b), the CD4$^+$ subpopulation of T cells (FIG. 7c), the CD8$^+$ subpopulation of T cells (FIG. 7d), and CD34$^+$ stem cells (FIG. 8), described below, cells derived from two patients. (Donor A and Donor B) were utilized.

TABLE 2

Conditions Employed for Studies Depicted in FIG. 7a

| Condition Number | Parameters |
|---|---|
| 1. | pA1CMVIX-CAT + DDAB:DOPE (1:1), DNA:liposome ratio (1:1). |
| 2. | pA1CMVIX-CAT + DDAB:DOPE (1:1), DNA:liposome ratio (1:2). |
| 3. | pA1CMVIX-CAT + DDAB:DOPE (1:2), DNA:liposome ratio (1:1). |
| 4. | pA1CMVIX-CAT + DDAB:DOPE (1:2), DNA:liposome ratio (1:2). |

TABLE 3

Conditions Employed for Studies Depicted in FIG. 7b–d

| Condition Number | Parameters |
|---|---|
| 1. | pA1CMVIX-CAT + DDAB:DOPE (1:1), DNA:liposome ratio (1:1). |
| 2. | pA1CMVIX-CAT + DDAB:DOPE (1:1), DNA:liposome ratio (1:2). |
| 3. | pA1CMVIX-CAT + DDAB:chol (1:1), DNA:liposome ratio (1:1). |
| 4. | pA1CMVIX-CAT + DDAB:chol (1:1), DNA:liposome ratio (1:2). |

For the studies depicted in FIGS. 7a–d, maximum levels of expression were observed on Days 2 and 3 in both total and purified subpopulations. Significant levels of expression were detected up to Day 14. The cells were harvested 3 days after transfection, and normalized protein content from each extract was analyzed for CAT activity. The same composition of liposome, and the DNA to liposome ratio induced similar levels of expression in all the populations.

G. Transgene expression induced by AAV plasmid:liposome complex in freshly isolated CD34$^+$ stem cells.

The effect of AAV plasmid:liposome complex in transfecting freshly isolated human peripheral blood CD34$^+$ stem cells was examined. The gene for chloramphenicol acetyl transferase (CAT) enzyme was used as the reporter gene in the pA1CMVIX-CAT plasmid (FIG. 1). The pA1CMVIX-CAT constructs were made, as described above. The level of CAT expression as determined by thin layer chromatography from CD34+ stem cells is set forth in FIG. 8.

TABLE 4

Conditions Employed for Studies Depicted in FIG. 8

| Condition Number | Parameters |
| --- | --- |
| 1. | pA1 CMV IX CAT + DDAB:DOPE (1:1) 1:1 DNA:liposome ratio. |
| 2. | pA1 CMV IX CAT + DDAB:DOPE (1:1) 1:2 DNA:liposome ratio. |

Freshly isolated CD34+ peripheral blood stem cells were transfected with AAV CAT plasmid DNA:liposome complexes. CD34+ cells were purified from peripheral blood using AIS CD34 MicroCELLectors after removing essentially all the T cells using CD5/8 MicroCELLector device. The stem cells were removed from the device and $0.5-1\times10^6$ cells were transfected with complexes comprising 10 micrograms of plasmid DNA and 10 nmoles of liposome. The transfected cells were cultured with medium containing stem cell factor, IL-3 and IL-1. On Day 3 and 7, the cells were harvested and extracts were made. Normalized protein content from the extract was assayed for CAT activity. As shown in FIG. 8., there were significant levels of CAT gene expression in the CD34+ peripheral blood stem cells.

H. Integration Studies.

FIGS. 9a–b illustrates enhanced chemiluminescence (ECL) Southern analyses of genomic DNA from stable clones (clones stable at least beyond Day 30) that were transfected with AAV plasmid DNA:liposome complexes in accordance with the invention. Genomic DNA was isolated and analyzed using the ECL direct nucleic acid labelling and detection system (Amersham). IL-2 probe was prepared from the 0.685 kb IL-2 gene from pACMV-IL2. After hybridization, the membrane was washed twice in 0.5x SSC/0.4% SDS at 55° C. for 10 minutes and twice in 2x SSC at room temperature for 5 minutes.

In FIG. 9a, samples were digested with Bam HI and Hind III and probed with IL-2. As shown in FIG. 9a, all clones showed the presence of the IL-2 gene, as demonstrated by the 0.685 kb band in Bam HI and Hind III digested genomic DNA.

For the data in FIG. 9b, samples were digested with Bam HI and probed with IL-2. Again, all clones showed IL-2 gene integration. (FIG. 9b) In FIG. 9b, integration of IL-2 was demonstrated by the high molecular weight bands (between 1.6 and 2 kb), bands which are consistent with integration of the gene in conjunction with attached host genomic material obtained via digestion. The data in FIG. 9b indicate that there was more than one integration site, since there were multiple high molecular weight bands in the Bam HI digested genomic DNA. Furthermore, the integration site was shown to be in different locations in different clones, as demonstrated by the different size bands in the digested clones (FIG. 9b).

FIGS. 10a–b depict chromosomal DNA analyses, using a $^{32}$P Southern assay, of two clones obtained from the present study. Nuclear DNA was isolated from the two IL-2 clones (1A11 and 1B11) using the Hirt fractionation protocol. As a negative control, total DNA was isolated from untransfected cells of the R3327 cell line. After restriction enzyme digestion, 10 micrograms of each sample, along with appropriate plasmid controls, were loaded onto a 1% agarose gel, electrophoresed, denatured and transferred onto Hybond+ membrane. The filters were hybridized overnight at 68° C. with DNA fragments labelled with $^{32}$P by random priming. The membranes were then washed at 68° C. for 2x 30 minutes each with 2x SSC, 0.1% SDS and 0.2x SSC, 0.1% SDS. Autoradiograms of these filters were exposed on x-ray film.

In FIG. 10a, the IL-2 gene was again used as the probe. Thus, after Southern blotting, the filter depicted in FIG. 10a was probed with a 0.68 kb IL2 Bam HI/Hind III fragment of pACMV-IL2. The data in FIG. 10a indicate that the number of copies of the IL-2 gene that integrated into a clone, varied from clone to clone; this finding was demonstrated by the various densities of the 0.685 kb band in the digests (as specified in the Brief Description of the Drawings) of cells of the two clones. Moreover, higher molecular weight bands were also demonstrated, which is consistent with integration of the IL-2 gene, together with host genomic material obtained from the various digest protocols.

For the data shown in FIG. 10b, the filter was probed with a 0.85 kb pvuII/HindIII (AAV ITR/CMV) fragment of the plasmid pACMV-IL2. The data in FIG. 10b indicate the presence of the right AAV ITR, as demonstrated by the 0.8 kb band in the smaI and pvuII digested chromosomal DNA. The presence of the left AAV ITR in one clone (clone A) was demonstrated by the 2.1 kb band in the smaI and pvuII digested chromosomal DNA.

III. EXAMPLES

A method in accordance with the invention, utilizing liposomes that comprise AAV viral material, is used to deliver genes for cytokines, costimulatory molecules such as B7, and molecules having MHC class I antigens into a wide variety of cell types. For example, such genomic material can be delivered into primary tumor cells, for tumor vaccines.

A method in accordance with the invention, comprising use of liposomes that contain AAV viral material, is used to deliver and express genes for substances such as peptides, anti-sense oligonucleotides, and RNA. Upon expression of such peptides, anti-sense oligonucleotides and RNA, a subject's immune response is modulated. The modulation of the immune response is either that of inducing the immune response or inhibiting the immune response. Accordingly, HIV infection is treated by using anti-sense oligonucleotides, RNA, or ribozymes that have been expressed by a method in accordance with the invention. Additionally, the immunologic response to a tumor is modulated by use of peptides or RNA expressed in accordance with the invention. A patient's immune response is modulated so as to respond to tumor-specific and/or tumor-associated antigens. Accordingly, non-immunogenic tumors are modified into immunogenic tumors which induce a cytolytic T cell response, both in vivo and in vitro.

A method in accordance with the invention is used to deliver genes to primary lymphoid cells, such as B cells or T cells. An alternate method in accordance with the invention is used to deliver genetic material to CD34+ stem cells. Accordingly, the genes are expressed and are used in therapy for conditions such as HIV infection, conditions of genetic defect, neoplasias, and auto-immune conditions, wherein expression a gene of interest is desired, as is appreciated by one of ordinary skill in the art. For example, for a malignant neoplastic condition, the MDR I gene is delivered in accordance with the invention, is expressed, and has therapeutic effect.

In a further example, CD8+ cells are selected with AIS MicroCELLectors. The source material for the CD8+ cells is peripheral blood for HIV patients, and tumor samples for patients with neoplasias. The T cells are then activated according to methods known in the art, such as by use of phytohemagglutinin (PHA). The activated cells are grown for 20 days. Thereafter, the cells are transfected in accordance with the invention with AAV:liposome complexes comprising IL-2 genomic material. The transfected cells are returned to the patient. Thus, the subsequent administration of IL-2 to a patient in order to maintain their cytotoxic T cell activity is reduced. Advantageously, the IL-2 gene, administered in accordance with the invention, permits lessened amounts of IL-2 to be provided systemically to a patient. Reducing the amount of IL-2 that is systemically administered is advantageous, since IL-2 displays potentially lethal dose-related toxicity.

IV. CONCLUSIONS

In the present studies, the AAV plasmid which contained transgene and AAV terminal repeats was used as a DNA vector, and cationic liposomes were used as carrier molecules. It was demonstrated that the AAV plasmid DNA:liposome complexes efficiently transfected primary tumor cells, cultured cell lines, primary lymphoid cells, and CD34+ stem cells. It was also demonstrated that, in the absence of any recombinant virus (producible from rep and cap capsid particles in adenoviral infected cells), integration with high level and sustained expression of transgene was achieved by the elegant transfection process.

In addition to high levels of expression, the combination of AAV plasmid:liposomes disclosed herein induced long-term (up to 30 days) expression of genes (FIGS. 3a and 3b), in contrast to the transient expression demonstrated by typical liposome-mediated transfection. Notably, sustained expression was demonstrated in the AAV plasmid lipofected group, as well as in the recombinant AAV transduced group (FIGS. 3a and 3b). Moreover, ten-fold higher levels of expression were observed with AAV plasmid as compared to standard plasmid transfection, as shown in FIGS. 2a and 2b.

Under the test conditions disclosed herein, there was no difference in efficiency between optimal AAV transduction and maximal AAV plasmid:liposome transfection. Concerning the time-course of expression, cationic liposomes had previously been shown to mediate only transient expression of standard plasmid DNA in mammalian cell types (Felgner, P. L., et al., "A highly efficient, lipid-mediated DNA transfection procedure," *Proc. Natl. Acad. Sci. USA* (1987) 84:7413–7417; Rose, J. K., et al., "A new cationic liposome reagent mediating nearly quantitative transfection of animal cells," *Biotechniques* (1991) 10:520–525). Moreover, concerning the efficiency of integration, much lower efficiency of integration into the host genome was observed in former liposome-mediated transfection as compared to the results disclosed herein (Shaefer-Ridder, M., et al., "Liposomes as gene carriers: Efficient transfection of mouse L cells by thymidine kinase gene," *Science* (1982) 215:166–168). As shown herein, however, cationic liposomes complexed with AAV plasmid DNA carrying the AAV terminal repeats increased the genomic DNA integration, relative to the standard plasmid that lacked only the AAV terminal repeats (ITRs). Liposomes comprising AAV plasmid material delivered the plasmid DNA in the absence of any specific cell surface receptors, and replaced the function of virus in gene delivery.

In the present studies, it was demonstrated that virus vectors can be altogether replaced by liposomes, and efficient expression and integration was attained by utilizing the construct, including the viral elements responsible for both the efficiency and integration. In this manner, production of virus for infection can be avoided, and there is no possibility of an adverse recombinant event. The end results were accomplished by use of an elegant transfection process combining AAV plasmid and cationic liposomes.

In a preferred embodiment, the combination of AAV plasmid and cationic liposomes not only transfected the cultured cell lines efficiently, but also transfected primary tumor cells and peripheral blood cells such as T cells and stem cells. These data are noteworthy since most gene therapy strategies involve gene delivery to primary T lymphocytes or tumor cells. Previously, these strategies have primarily relied upon transgene insertion into retroviral or DNA virus vectors (Dimmock, N.J., "Initial stages in infection with animal viruses," *J. Gen. Virol:* (1982) 59:1–22; Duc-Nguyen, H., "Enhancing effect of diethylaminoethyl dextran on the focus forming titer of a murine sarcoma virus (Harvey strain)," *J. Virol.* (1968) 2:643–644). A fundamental disadvantage of the retroviral system is understood to be the inability to transfect non-dividing primary cells (Innes, C. L., et al., "Cationic liposomes (lipofectin) mediate retroviral infection in the absence of specific receptors," *J. Virol.* (1990) 64:957–961). In contrast, for the first time in the art, the present studies have shown that cationic liposomes comprising AAV material mediated transfection of both dividing and non-dividing cell types. In accordance with the invention, AAV plasmid:cationic liposomes have provided a highly efficient transfection system that achieved sustained, high-level expression.

Advantageously, plasmid DNA:liposome complexes can be delivered in vivo (such as by intravenous, intraperitoneal and aerosol administration) without any measurable toxicity (Philip, R., et al., "In vivo gene delivery: Efficient transfection of T lymphocytes in adult mice," *J. Biol. Chem.* (1993) 268:16087–16090; Stribling, R., et al., "Aerosol Gene Delivery in vivo," *Proc. Natl. Acad. Sci. USA* (1992) 89:11277–11281; Zhu, N., et al., "Systemic gene expression after intravenous DNA delivery into adult mice," *Science* (1993) 261:209–211; Stewart, M. J., et al., "Gene transfer in vivo with DNA-liposome complexes: Safety and acute toxicity in mice," *Human Gene Therapy* (1992) 3:267–275). In accordance with the invention, DNA concentration can be optimized to obtain maximum expression. Thus, gene transfer by use of liposomes comprising AAV material transferred AAV and transgene material into a wide variety of cell types ex vivo, and is of use in vivo as well. These present results are of immense advantage to any gene therapy protocol.

As used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

What is claimed is:

1. A T cell transfected by a composition for genetic manipulation, said composition comprising:
   a cationic liposome; and
   a double-stranded circular plasmid DNA vector lacking a selectable marker and encoding at least one inverted terminal repeat from adeno-associated virus, a promoter other than an adeno-associated virus promoter and a genetic sequence of interest.

2. The transfected cell of claim 1 wherein said cell is a $CD3^+$, $CD4^+$, or $CD8^+$ T cell.

3. The transfected cell of claim 1 wherein said genetic sequence of interest is the gene encoding IL-2.

4. A T cell transfected by a method of introducing a genetic sequence of interest into a host cell, said method comprising steps of;
   providing a composition comprising a cationic liposome; and
   a double-stranded circular plasmid DNA lacking a selectable marker and encoding at least one inverted terminal repeat from adeno-associated virus, a promoter other than an adeno-associated virus promoter and a genetic sequence of interest; and
   contacting said composition with a host cell whereby the genetic sequence of interest is introduced into the host cell.

5. The transfected cell of claim 4 wherein the host cell is $CD3^+$, $CD4^+$, or $CD8^+$ T cell.

* * * * *